(12) United States Patent
Nathwani et al.

(10) Patent No.: US 11,344,608 B2
(45) Date of Patent: *May 31, 2022

(54) FACTOR IX GENE THERAPY

(71) Applicant: UCL Business LTD, London (GB)

(72) Inventors: Amit Nathwani, London (GB); Jenny Mcintosh, London (GB); Nishil Patel, London (GB)

(73) Assignee: UCL BUSINESS LTD, London (GB)

( * ) Notice: Subject to any disclaimer, the term of this patent is extended or adjusted under 35 U.S.C. 154(b) by 294 days.

This patent is subject to a terminal disclaimer.

(21) Appl. No.: 16/563,193

(22) Filed: Sep. 6, 2019

(65) Prior Publication Data

US 2019/0388523 A1 Dec. 26, 2019

Related U.S. Application Data

(63) Continuation of application No. 15/525,836, filed as application No. PCT/GB2015/053438 on Nov. 12, 2015, now Pat. No. 10,413,598.

(30) Foreign Application Priority Data

Nov. 12, 2014 (GB) ..................................... 1420139

(51) Int. Cl.
| | | |
|---|---|---|
| *A61K 48/00* | (2006.01) | |
| *C07H 21/04* | (2006.01) | |
| *A61K 38/48* | (2006.01) | |
| *C12N 9/64* | (2006.01) | |
| *A61P 7/04* | (2006.01) | |
| *A61K 38/27* | (2006.01) | |
| *C12N 9/50* | (2006.01) | |
| *C12N 15/113* | (2010.01) | |
| *C12N 15/62* | (2006.01) | |
| *C12N 15/85* | (2006.01) | |
| *C12N 15/79* | (2006.01) | |

(52) U.S. Cl.
CPC .......... *A61K 38/4846* (2013.01); *A61K 38/27* (2013.01); *A61P 7/04* (2018.01); *C12N 9/50* (2013.01); *C12N 9/644* (2013.01); *C12N 15/113* (2013.01); *C12N 15/62* (2013.01); *C12N 15/85* (2013.01); *C12Y 304/21022* (2013.01); *C07H 21/04* (2013.01); *C12N 15/79* (2013.01)

(58) Field of Classification Search
CPC ....... C12N 5/10; C12N 2510/00; C07H 21/04
See application file for complete search history.

(56) References Cited

U.S. PATENT DOCUMENTS

| 6,271,025 B1 | 8/2001 | Negrier et al. |
|---|---|---|
| 6,419,921 B1 | 7/2002 | Negrier et al. |
| 6,723,551 B2 | 4/2004 | Kotin et al. |
| 6,800,461 B2 | 10/2004 | Negrier et al. |
| 6,884,616 B1 | 4/2005 | Negrier et al. |
| 8,198,421 B2 | 6/2012 | Samulski |
| 2002/0076798 A1 | 6/2002 | Miao et al. |
| 2002/0086427 A1 | 7/2002 | Leiden et al. |
| 2003/0022378 A1 | 1/2003 | Ehrhardt et al. |
| 2003/0130221 A1 | 7/2003 | High et al. |
| 2003/0148506 A1 | 8/2003 | Kotin et al. |
| 2003/0186291 A1 | 10/2003 | Faust et al. |
| 2004/0053870 A1 | 3/2004 | Yew et al. |
| 2007/0000352 A1 | 1/2007 | Itoh |
| 2007/0180546 A1 | 8/2007 | Rapp et al. |
| 2008/0153156 A1 | 6/2008 | Gray |
| 2008/0269125 A1 | 10/2008 | Ballance et al. |
| 2008/0305991 A1 | 12/2008 | DeFrees et al. |
| 2011/0070241 A1 | 3/2011 | Yang |
| 2011/0287532 A1 | 11/2011 | Gray |
| 2012/0009222 A1 | 1/2012 | Nguyen et al. |
| 2013/0236974 A1 | 9/2013 | de Fougerolles |
| 2014/0107186 A1 | 4/2014 | Garcia et al. |
| 2014/0271550 A1 | 9/2014 | Rabinowitz et al. |
| 2015/0023924 A1 | 1/2015 | High et al. |
| 2016/0122739 A1 | 5/2016 | Sheehan et al. |
| 2016/0222414 A1 | 8/2016 | Rabinowitz et al. |
| 2016/0361427 A1 | 12/2016 | Defrees et al. |
| 2016/0375110 A1 | 12/2016 | High et al. |

(Continued)

FOREIGN PATENT DOCUMENTS

| CN | 106497949 A | 3/2017 |
|---|---|---|
| EP | 1010762 A1 | 6/2000 |
| EP | 1026250 A1 | 8/2000 |

(Continued)

OTHER PUBLICATIONS

Binny et al., 2012 "Vector Systems for Prenatal Gene Therapy: Principles of Adeno-Associated Virus Vector Design and Production" Methods in Molecular Biology, Apr. 25, 2012 pp. 109-131 vol. 891.

(Continued)

*Primary Examiner* — Shin Lin Chen

(74) *Attorney, Agent, or Firm* — Wilson Sonsini Goodrich & Rosati

(57) ABSTRACT

The invention relates to a new, more potent, coagulation Factor IX (FIX) expression cassette for gene therapy of Haemophilia B (HB). Disclosed is a vector for expressing factor IX protein, the vector comprising a promoter, a nucleotide sequence encoding for a functional factor IX protein, and an intron sequence, wherein the intron sequence is positioned between exon 1 and exon 2 of the nucleotide sequence encoding for a functional factor IX protein, and wherein the intron sequence has at least 80% identity to the sequence of SEQ ID NO. 1 as disclosed herein.

14 Claims, 3 Drawing Sheets

Figure 1:
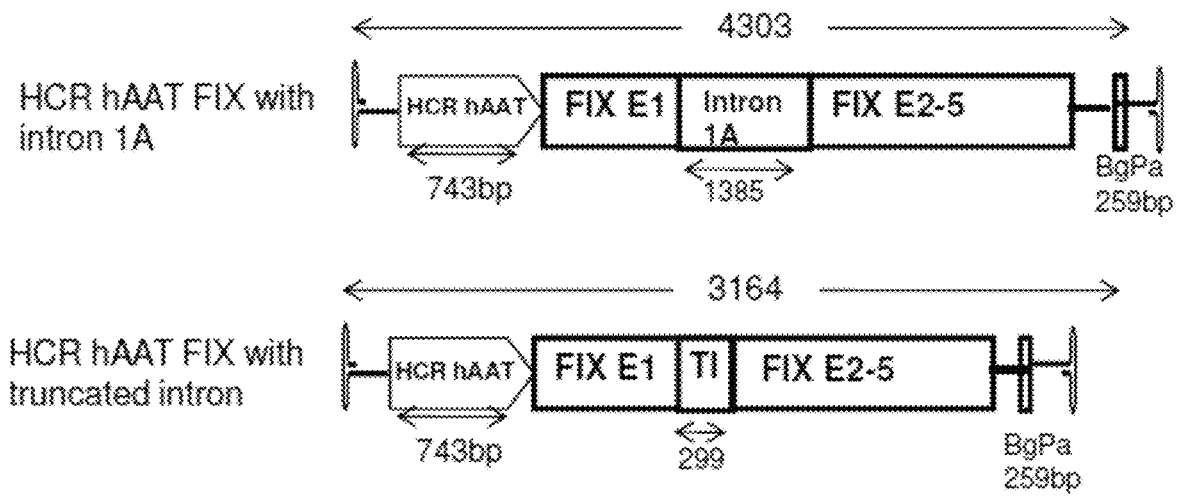

Specification includes a Sequence Listing.

(56) References Cited

U.S. PATENT DOCUMENTS

2017/0136104 A1   5/2017   Defrees et al.

FOREIGN PATENT DOCUMENTS

| | | |
|---|---|---|
| EP | 1038959 A1 | 9/2000 |
| EP | 1048726 A2 | 11/2000 |
| EP | 1048735 A1 | 11/2000 |
| EP | 1048736 A1 | 11/2000 |
| EP | 2067488 A1 | 6/2009 |
| EP | 2216409 A1 | 8/2010 |
| EP | 2394667 | 12/2011 |
| EP | 2492347 | 8/2012 |
| WO | 9742900 A1 | 11/1997 |
| WO | 9841240 A1 | 9/1998 |
| WO | 9903496 A1 | 1/1999 |
| WO | 9949803 A1 | 10/1999 |
| WO | WO-9949880 | 10/1999 |
| WO | 0014262 A2 | 3/2000 |
| WO | WO-0049147 | 8/2000 |
| WO | WO-0054787 | 9/2000 |
| WO | 0136620 A2 | 5/2001 |
| WO | 0166149 A2 | 9/2001 |
| WO | 0170763 A1 | 9/2001 |
| WO | 0175092 A2 | 10/2001 |
| WO | 0179271 A1 | 10/2001 |
| WO | WO-2001077137 | 10/2001 |
| WO | 0198482 A2 | 12/2001 |
| WO | WO-0170968 | 12/2001 |
| WO | 0240544 A2 | 5/2002 |
| WO | WO-0234296 | 5/2002 |
| WO | 02062376 A1 | 8/2002 |
| WO | 02062377 A2 | 8/2002 |
| WO | 02064799 A2 | 8/2002 |
| WO | 02071843 A1 | 9/2002 |
| WO | 02079447 A2 | 10/2002 |
| WO | 03020764 A2 | 3/2003 |
| WO | 03025146 A2 | 3/2003 |
| WO | 03048364 A2 | 6/2003 |
| WO | WO-02099105 | 8/2003 |
| WO | WO-2004027019 | 8/2004 |
| WO | 2004080162 A2 | 9/2004 |
| WO | 2004092351 A2 | 10/2004 |
| WO | 2005040215 A2 | 5/2005 |
| WO | WO-2005037226 | 7/2005 |
| WO | 2005084430 A1 | 9/2005 |
| WO | WO-2004098532 | 1/2006 |
| WO | 2006018204 A1 | 2/2006 |
| WO | 2006026238 A2 | 3/2006 |
| WO | 2006036502 A2 | 4/2006 |
| WO | WO-2005058283 | 5/2006 |
| WO | WO-2006015789 | 6/2006 |
| WO | 2006093847 A1 | 9/2006 |
| WO | WO-2006103258 | 10/2006 |
| WO | 2006127896 A2 | 11/2006 |
| WO | 2007046703 A2 | 4/2007 |
| WO | 2007047706 A2 | 4/2007 |
| WO | WO-2006110689 | 4/2007 |
| WO | WO-2007036233 | 6/2007 |
| WO | 2007120533 A2 | 10/2007 |
| WO | 2007130453 A2 | 11/2007 |
| WO | 2007135182 A2 | 11/2007 |
| WO | 2007148971 A2 | 12/2007 |
| WO | 2007149406 A2 | 12/2007 |
| WO | 2007149852 A2 | 12/2007 |
| WO | 2008091311 A1 | 7/2008 |
| WO | WO-2007120542 | 7/2008 |
| WO | 2008092643 A2 | 8/2008 |
| WO | 2008092644 A2 | 8/2008 |
| WO | 2008124724 A1 | 10/2008 |
| WO | 2008153366 A2 | 12/2008 |
| WO | 2009014445 A2 | 1/2009 |
| WO | 2009026393 A2 | 2/2009 |
| WO | 2009038462 A1 | 3/2009 |
| WO | 2009051717 A2 | 4/2009 |
| WO | 2009059056 A2 | 5/2009 |
| WO | 2009061369 A2 | 5/2009 |
| WO | 2009102085 A1 | 8/2009 |
| WO | WO-2009102085 | 8/2009 |
| WO | 2009130198 A2 | 10/2009 |
| WO | 2009137254 A2 | 11/2009 |
| WO | 2009140015 A2 | 11/2009 |
| WO | WO-2008118507 | 12/2009 |
| WO | 2010012451 A1 | 2/2010 |
| WO | 2010029178 A1 | 3/2010 |
| WO | 2010055413 A1 | 5/2010 |
| WO | 2011005968 A1 | 1/2011 |
| WO | 2011014890 A1 | 2/2011 |
| WO | WO-2011011841 | 2/2011 |
| WO | 2011054994 A1 | 5/2011 |
| WO | 2011122950 A1 | 10/2011 |
| WO | 2011154520 A1 | 12/2011 |
| WO | WO-2011133933 | 1/2012 |
| WO | 2012061654 A1 | 5/2012 |
| WO | 2012135805 A2 | 10/2012 |
| WO | WO-2011133890 | 3/2013 |
| WO | WO-2013078316 | 5/2013 |
| WO | WO-2013078400 | 5/2013 |
| WO | 2013090648 A1 | 6/2013 |
| WO | WO-2013123457 | 8/2013 |
| WO | WO-2013123503 | 8/2013 |
| WO | WO-2013158879 | 10/2013 |
| WO | 2013173512 A2 | 11/2013 |
| WO | 2014016580 A1 | 1/2014 |
| WO | WO-2012170930 | 1/2014 |
| WO | 2014063108 A1 | 4/2014 |
| WO | 2014063753 A1 | 5/2014 |
| WO | 2014064277 A1 | 5/2014 |
| WO | 2014070349 A2 | 5/2014 |
| WO | 2014081831 A1 | 5/2014 |
| WO | 2014152940 A1 | 9/2014 |
| WO | 2014193716 A2 | 12/2014 |
| WO | 2015012924 A2 | 1/2015 |
| WO | 2015013313 A2 | 1/2015 |
| WO | WO-2015038625 | 3/2015 |
| WO | 2015073988 A1 | 5/2015 |
| WO | 2015086406 A2 | 6/2015 |
| WO | WO-2014182684 | 6/2015 |
| WO | WO-2015054439 | 6/2015 |
| WO | WO-2015085276 | 6/2015 |
| WO | WO-2015099513 | 7/2015 |
| WO | 2015139093 A1 | 9/2015 |
| WO | 2015162302 A2 | 10/2015 |
| WO | 2016004113 A1 | 1/2016 |
| WO | 2016028872 A2 | 2/2016 |
| WO | WO-2016041588 | 3/2016 |
| WO | 2016073837 A1 | 5/2016 |
| WO | 2016075473 A2 | 5/2016 |
| WO | WO-2016127057 | 8/2016 |
| WO | 2016146757 A1 | 9/2016 |
| WO | 2016179644 A1 | 11/2016 |
| WO | WO-2016168728 | 11/2016 |
| WO | WO-2016181122 | 11/2016 |
| WO | WO-2016181123 | 11/2016 |
| WO | 2016210170 A1 | 12/2016 |
| WO | WO-2017011519 | 1/2017 |
| WO | 2017024060 A1 | 2/2017 |
| WO | WO-2017021359 | 2/2017 |
| WO | 2017070167 A1 | 4/2017 |
| WO | WO-2017074526 | 5/2017 |
| WO | 2017096039 A1 | 6/2017 |
| WO | WO-2018213786 | 11/2018 |
| WO | WO-2018217731 | 11/2018 |
| WO | WO-2018222792 | 12/2018 |

OTHER PUBLICATIONS

Kao C Y et al., 2013 "Incorporation of the factor IX Padua mutation into FIX-Triple improves clotting activity in vitro and in vivo" Thrombosis and Haemostasis, May 16, 2013 pp. 244-256 vol. 110 No. 2.

Wang et al., 1997 "A factor IX-deficient Mouse Model of hemophilia B gene therapy". Proceeding of the National Academy of

(56) References Cited

OTHER PUBLICATIONS

Sciences of the United States of America, 1997 pp. 11563-11566 vol. 94.

Allan, et al. Evolutionary Duplication of a Hepatic Control Region in the Human Apolipoprotein E Gene Locus. Identification of a Second Region That Confers High Level and Liver-Specific Expression of the Human Apolipoprotein E Gene in Transgenic Mice. The Journal of Biological Chemistry. vol. 270 No. 44, 1995. pp. 26278-26281.

Altschul, et al., Basic Local Alignment Search Tool. 1990, J. Mol. Biol. 215, pp. 403-410.

Altschul, et al., Gapped BLAST and PSI-BLAST: a New Generation of Protein Database Search Programs. 1997, Nucleic Acids Research, 25(17), pp. 3389-3402.

Arruda, et al. Emerging Therapies for Hemophilia: Controversies and Unanswered Questions. F1000research. 7, 2018. 489.

Bantel-Schaal et al., Human Adeno-Associated Virus Type 5 Is Only Distantly Related to Other Known Primate Helper-Dependent Parvoviruses. 1999, Journal of Virology, 73(2), pp. 939-947.

Berns, et al. "Parvoviridae: The Viruses and Their Replication," Chapter 69 in Fields Virology (3d Ed. 1996).

Bryan et al., Implications of Protein Fold Switching. Current Comments, 2013, http://www.elsevierblogs.com/currentcomments/p=962. Implications of protein fold switching, p. 1-4.

Cantore et al, Blood, "Hyperfunctional Coagulation factor IX improves The Efficacy of Gene Therapy in Hemophilic Mice" 2012, vol. 120, pp. 4517-4520.

Chiorini, et al. Cloning and Characterization of Adeno-Associated Virus Type 5. Journal of Virology. 73.2 (1999): 1309-1319.

Chiorini, et al. Cloning of Adeno-Associated Virus Type 4 (aav4) and Generation of Recombinant Aav4 Particles. Journal of Virology. 71.9 (1997): 6823.

Dang, et al. In Vivo Footprinting Analysis of the Hepatic Control Region of the Human Apolipoprotein E/c-I/c-Iv/c-Ii Gene Locus. Journal of Biological Chemistry. 271.45 (1996): 28667-28676.

Dang, et al. Structure of the Hepatic Control Region of the Human Apolipoprotein E/c-I Gene Locus. Journal of Biological Chemistry. 270.38 (1995): 22577-22585.

Dunbar et al., Gene Therapy Comes of Age. Science, vol. 359, 175 (2018) Jan. 12, 2018. 4672, p. 1-10.

Enjolras et al., The Three In-frame ATG, Clustered in the Translation Initiation Sequence of Human Factor IX Gene, Are Required for an Optimal Protein Production, Thrombosis and Haemostasis, Schattauer GMBH Germany, Oct. 1, 1999, pp. 1264-1269, vol. 82, No. 4.

Fagone et al., Systemic Errors in Quantitative Polymerase Chain Reaction Titration of Self-Complementary Adeno-Associated Viral Vectors and Improved Alternative Methods Human Gene Therapy Methods. Feb. 23, 2012 (1):1-7.

Haas et al. Codon Usage Limitation in the Expression of Hiv-1 Envelope Glycoprotein. Current Biology. 6.3 (1996): 315-324.

Hafenrichter, et al. Quantitative Evaluation of Liver-Specific Promoters from Retroviral Vectors After in Vivo Transduction of Hepatocytes. Blood. 84.10 (1994): 3394.

Intellectual Property Office Search Report, Application No. GB1420139. 6, dated Jul. 31, 2015, 5 pages.

Kaur et al., Addressing the Challenge: Current and Future Directions in Ovarian Cancer Therapy. (2009) Current Gene Therapy, vol. 9. p. 434-458.

Kurachi et al., Role of Intron I in Expression of the Human Factor IX Gene, Journal of Biological Chemistry, American Society for Biochemistry and Molecular Biology, US, Mar. 10, 1995, pp. 5276-5281, vol. 270, No. 10.

Lenzi et al., NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), 2014, pp. 1-16.

Maqbool et al., The Substrate-binding Protein in Bacterial ABC Transporters: Dissecting Roles in the Evolution of Substrate Specificity. 2015, Biochemical Society Transactions, vol. 43, No. 5, p. 1011-1017.

Mcintosh et al., Therapeutic Levels of FVIII Following A Single Peripheral Vein Administration of rAAV Vector Encoding A Novel Human Factor VIII Variant, Blood, American Society of Hematology, US, Apr. 25, 2013, pp. 3335-3344, vol. 121, No. 17.

Miao, et al. Inclusion of the Hepatic Locus Control Region, an Intron, and Untranslated Region Increases and Stabilizes Hepatic Factor Ix Gene Expression in Vivo but Not in Vitro. Molecular Therapy. 1.6 (2000): 522-532.

Nathwani et al., Adenovirus-Associated Virus Vector-Mediated Gene Transfer in Hemophilia B, New England Journal of Medicine, Dec. 22, 2011, pp. 2357-2365, vol. 365, No. 25.

Nathwani et al., Our Journey to Successful Gene Therapy for Hemophilia B, Human Gene Therapy, Nov. 1, 2014, pp. 923-926, vol. 25, No. 11.

Nathwani, et al. Gene Therapy—Self-Complementary Adeno-Associated Virus Vectors Containing a Novel Liver-Specific Human Factor Ix Expression Cassette Enable Highly Efficient Transduction of Murine and Nonhuman Primate Liver. Blood. 107.7 (2006): 2653.

Nathwani, et al., Long-Term Safety and Efficacy Following Systemic Administration of a Self-Complementary AAV Vector Encoding Human FIX Pseudotyped With Serotype 5 and 8 Capsid Proteings. Molecular Therapy. May 19, 2011. (5):876-85.

Needleman, et al. A General Method Applicable to the Search for Similarities in the Amino Acid Sequence of Two Proteins. Journal of Molecular Biology. 48.3 (1970): 443-453.

Okuyama, et al. Liver-directed Gene Therapy: a Retroviral Vector with a Complete Ltr and the Apoe Enhancer a1 Antitrypsin Promoter Dramatically Increases Expression of Human a1 Antitrypsin in Vivo. Human Gene Therapy. 7.5 (1996): pp. 637-645.

PCT International Search Report and Written Opinion, PCT/GB2015/053438, dated Jul. 5, 2016, 18 pages.

Plantier et al., A factor VIII Minigene Comprising the Truncated Intron I of Factor IX highly Improves the In Vitro Production of Factor VIII. Thromb Haemost, 2001; vol. 86, pp. 596-603.

Rodriguez et al.—Biosynthesis of FVIII in megakaryocytic cells: improved production and biochemical characterization. British Journal of Haematology. 5.127 Dec. 2004: 568-575.

Rutledge, et al. Infectious Clones and Vectors Derived from Adeno-Associated Virus (aav) Serotypes Other Than Aav Type 2. Journal of Virology. 72.1 (1998): 309-319.

Shim et al., Nonviral Delivery System for Cancer Gene Therapy: Strategies and Challenges. 2017, Current Gene Therapy, vol. 17, No. 5, p. 1-18.

Srivastava, et al. Nucleotide Sequence and Organization of the Adeno-Associated Virus 2 Genome. Journal of Virology. 45.2 (1983): pp. 555-564.

Suwanmaneee et al., Integration-deficient Lentiviral Vectors Expressing Codon-optimized R338L Human FIX Restore Normal Hemostasis in Hemophilia B Mice. The American Society of Gene Cell Therapy, Mar. 2014; doi:10.1038/mt.2013.188. Molecular Therapy vol. 22, No. 3, 567-574.

Wang, et al. Sustained Correction of Bleeding Disorder in Hemophilia B Mice by Gene Therapy. Proceedings of the National Academy of Sciences. 96.7 (1999): 3906-3910.

Welch, et al. Youre One in a Googol: Optimizing Genes for Protein Expression. Journal of the Royal Society Interface. 6 (2009).

Wooddell et al.—Sustained Liver-Specific Transgene Expression from the Albumin Promoter in Mice Following Hydrodynamic Plasmid Dna Delivery. Journal of Gene Medicine. 10.5 (2008): 551-563.

Wu et al., Optimization of Self-Complementary AAV Vectors for Liver-Directed Expression Results in Sustained Correction of Hemophilia B at Low Vector Dose. Molecular Therapy Feb. 2008;16(2):280-9.

Wu, et al. Mutational Analysis of the Adeno-Associated Virus Type 2 (aav2) Capsid Gene and Construction of Aav2 Vectors with Altered Tropism. Journal of Virology 74.18 (2000): pp. 8635-8647.

SEQUENCE LISTING

```
<160> NUMBER OF SEQ ID NOS: 6

<210> SEQ ID NO 1
<211> LENGTH: 299
<212> TYPE: DNA
<213> ORGANISM: Artificial sequence
<220> FEATURE:
<223> OTHER INFORMATION: Nucleotide sequence of truncated intron (TI)

<400> SEQUENCE: 1
gtttgtttcc ttttttaaaa tacattgagt atgcttgcct tttagatata gaaatatctg      60
atgctgtctt cttcactaaa ttttgattac atgatttgac agcaatattg aagagtctaa     120
cagccagcac gcaggttggt aagtactgtg ggaacatcac agattttggc tccatgccct     180
aaagagaaat tggctttcag attatttgga ttaaaaacaa agactttctt aagagatgta     240
aaattttcat gatgttttct tttttgctaa aactaaagaa ttattctttt acatttcag      299

<210> SEQ ID NO 2
<211> LENGTH: 1386
<212> TYPE: DNA
<213> ORGANISM: Artificial sequence
<220> FEATURE:
<223> OTHER INFORMATION: Nucleotide sequence of codon optimised FIX

<400> SEQUENCE: 2
atgcagcgcg tgaacatgat catggcagaa tcaccaggcc tcatcaccat ctgccttta      60 ggatatctac tcagtgctga atgtacagtt tttcttgatc atgaaaacgc caacaaaatt     120
ctgaatcggc caaagaggta taattcaggt aaattggaag agtttgttca agggaacctt     180
gagagagaat gtatggagga gaagtgttct ttcgaggagg cgagagaggt tttcgagaat     240
actgagcgaa caaccgaatt ctggaaacaa tatgtggatg gcgaccaatg tgaatctaat     300
ccctgcctca acggtggctc atgcaaagac gatatcaaca gctacgagtg ttggtgcccc     360
tttggtttcg agggaaagaa ttgcgagctt gatgtaacct gtaacattaa gaatgggcgc     420
tgcgaacagt tttgcaagaa cagcgccgac aataaggtcg tctgcagttg taccgaaggc     480
tataggcttg cagagaatca gaagagttgc gagcctgctg tgccgttccc atgtggcaga     540
gtcagtgtgt cccaaactag caagctgaca agagcagaag ccgttttccc cgatgtggac     600
tacgtgaatt ccactgaagc cgaaacgatc ctggacaata tcacacagag cactcagtct     660
ttcaacgact tcacacgggt tgtgggagga gaggacgcca aacccggcca gtttccttgg     720
```

| | |
|---|---|
| caagtcgttc ttaacggcaa ggtcgacgcc ttttgtggag ggagtattgt gaacgagaaa | 780 |
| tggattgtca ccgctgctca ttgtgttgaa actggggtga aaatcactgt tgtcgcagga | 840 |
| gagcacaata tcgaagagac agaacacacc gagcagaaac gcaacgttat tcggatcatt | 900 |
| ccacatcaca actacaatgc tgccatcaac aagtacaacc acgacattgc gctgctggag | 960 |
| ttggatgaac ctctcgtgct caactcctat gtgaccccaa tctgcatagc agataaggag | 1020 |
| tataccaaca tcttcctgaa gtttgggtca ggttatgtgt caggctgggg acgagtgttt | 1080 |
| cataaaggga gatcagcact ggtgttgcag tatctgcgcg taccactggt ggatcgggct | 1140 |
| acttgcctgc gtagcacaaa attcaccatc tacaacaaca tgttttgtgc cggttttcac | 1200 |
| gaaggcggca gggacagctg tcagggagat tccggagggc ctcatgtcac agaggtcgag | 1260 |
| ggcacctcct ttctcactgg gattataagc tggggagaag aatgcgccat gaaagggaag | 1320 |
| tacggcatat acacgaaagt gtctagatac gtgaattgga ttaaggaaaa gaccaaactg | 1380 |
| acgtga | 1386 |

<210> SEQ ID NO 3
<211> LENGTH: 1685
<212> TYPE: DNA
<213> ORGANISM: Artificial sequence
<220> FEATURE:
<223> OTHER INFORMATION: Nucleotide sequence of codon optimised FIX
      containing truncated intron (TI)

<400> SEQUENCE: 3

| | |
|---|---|
| atgcagcgcg tgaacatgat catggcagaa tcaccaggcc tcatcaccat ctgccttta | 60 |
| ggatatctac tcagtgctga atgtacaggt ttgtttcctt ttttaaaata cattgagtat | 120 |
| gcttgccttt tagatataga aatatctgat gctgtcttct tcactaaatt ttgattacat | 180 |
| gatttgacag caatattgaa gagtctaaca gccagcacgc aggttggtaa gtactgtggg | 240 |
| aacatcacag attttggctc catgccctaa agagaaattg ctttcagat tatttggatt | 300 |
| aaaaacaaag actttcttaa gagatgtaaa attttcatga tgtttcttt tttgctaaaa | 360 |
| ctaaagaatt attcttttac atttcagttt ttcttgatca tgaaaacgcc aacaaaattc | 420 |
| tgaatcggcc aaagaggtat aattcaggta aattggaaga gtttgttcaa gggaaccttg | 480 |
| agagagaatg tatggaggag aagtgttctt cgaggaggc gagagaggtt ttcgagaata | 540 |
| ctgagcgaac aaccgaattc tggaaacaat atgtggatgg cgaccaatgt gaatctaatc | 600 |
| cctgcctcaa cggtggctca tgcaaagacg atatcaacag ctacgagtgt tggtgcccct | 660 |
| ttggtttcga gggaaagaat tgcgagcttg atgtaacctg taacattaag aatgggcgct | 720 |
| gcgaacagtt ttgcaagaac agcgccgaca ataaggtcgt ctgcagttgt accgaaggct | 780 |
| ataggcttgc agagaatcag aagagttgcg agcctgctgt gccgttccca tgtggcagag | 840 |
| tcagtgtgtc ccaaactagc aagctgacaa gagcagaagc cgttttcccc gatgtggact | 900 |
| acgtgaattc cactgaagcc gaaacgatcc tggacaatat cacacagagc actcagtctt | 960 |
| tcaacgactt cacacgggtt gtgggaggag aggacgccaa acccggccag tttccttggc | 1020 |
| aagtcgttct taacggcaag gtcgacgcct tttgtggagg gagtattgtg aacgagaaat | 1080 |
| ggattgtcac cgctgctcat tgtgttgaaa ctggggtgaa atcactgtt gtcgcaggag | 1140 |
| agcacaatat cgaagagaca gaacacaccg agcagaaacg caacgttatt cggatcattc | 1200 |
| cacatcacaa ctacaatgct gccatcaaca agtacaacca cgacattgcg ctgctggagt | 1260 |
| tggatgaacc tctcgtgctc aactcctatg tgaccccaat ctgcatagca gataaggagt | 1320 |

```
ataccaacat cttcctgaag tttgggtcag gttatgtgtc aggctgggga cgagtgtttc      1380
ataaagggag atcagcactg gtgttgcagt atctgcgcgt accactggtg gatcgggcta      1440
cttgcctgcg tagcacaaaa ttcaccatct acaacaacat gttttgtgcc ggttttcacg      1500
aaggcggcag ggacagctgt cagggagatt ccggagggcc tcatgtcaca gaggtcgagg      1560
gcacctcctt tctcactggg attataagct ggggagaaga atgcgccatg aaagggaagt      1620
acggcatata cacgaaagtg tctagatacg tgaattggat taaggaaaag accaaactga      1680
cgtga                                                                  1685

<210> SEQ ID NO 4
<211> LENGTH: 354
<212> TYPE: DNA
<213> ORGANISM: Artificial sequence
<220> FEATURE:
<223> OTHER INFORMATION: Nucleotide sequence of promoter HLP2

<400> SEQUENCE: 4
ccctaaaatg gcaaacatt gcaagcagca aacagcaaac acacagccct ccctgcctgc        60
tgaccttgga gctggggcag aggtcagaca cctctctggg cccatgccac ctccaactgg      120
acacaggacg ctgtggtttc tgagccaggg ggcgactcag atcccagcca gtggacttag      180 ccctgtttg ctcctccgat aactggggtg accttggtta atattcacca gcagcctccc       240
ccgttgcccc tctggatcca ctgcttaaat acggacgagg acagggccct gtctcctcag      300
cttcaggcac caccactgac ctgggacagt gaatgatccc cctgatctgc ggcc            354

<210> SEQ ID NO 5
<211> LENGTH: 2383
<212> TYPE: DNA
<213> ORGANISM: Artificial sequence
<220> FEATURE:
<223> OTHER INFORMATION: Nucleotide sequence of HLP2 FIX TI vector

<400> SEQUENCE: 5
ccctaaaatg gcaaacatt gcaagcagca aacagcaaac acacagccct ccctgcctgc        60
tgaccttgga gctggggcag aggtcagaca cctctctggg cccatgccac ctccaactgg      120
acacaggacg ctgtggtttc tgagccaggg ggcgactcag atcccagcca gtggacttag      180 ccctgtttg ctcctccgat aactggggtg accttggtta atattcacca gcagcctccc       240
ccgttgcccc tctggatcca ctgcttaaat acggacgagg acagggccct gtctcctcag      300
cttcaggcac caccactgac ctgggacagt gaatgatccc cctgatctgc ggcctcgacg      360
gtatcgataa gcttgatatc gaattctagt cgtcgaccac tttcacaatc tgctagcaaa      420
ggttatgcag cgcgtgaaca tgatcatggc agaatcacca ggcctcatca ccatctgcct      480
tttaggatat ctactcagtg ctgaatgtac aggtttgttt cctttttaa aatacattga       540 gtatgcttgc cttttagata tagaaatatc tgatgctgtc ttcttcacta aattttgatt      600
acatgatttg acagcaatat tgaagagtct aacagccagc acgcaggttg gtaagtactg      660
tgggaacatc acagattttg gctccatgcc ctaaagagaa attggctttc agattatttg      720
gattaaaaac aaagactttc ttaagagatg taaaattttc atgatgtttt cttttttgct      780
aaaactaaag aattattctt ttacatttca gttttttcttg atcatgaaaa cgccaacaaa      840
attctgaatc ggccaaagag gtataattca ggtaaattgg aagagtttgt tcaagggaac      900
cttgagagag aatgtatgga ggagaagtgt ttctttcgagg aggcgagaga ggttttcgag      960
aatactgagc gaacaaccga attctggaaa caatatgtgg atggcgacca atgtgaatct     1020
```

```
aatccctgcc tcaacggtgg ctcatgcaaa gacgatatca acagctacga gtgttggtgc      1080
ccctttggtt tcgagggaaa gaattgcgag cttgatgtaa cctgtaacat taagaatggg      1140
cgctgcgaac agttttgcaa gaacagcgcc gacaataagg tcgtctgcag ttgtaccgaa      1200
ggctataggc ttgcagagaa tcagaagagt tgcgagcctg ctgtgccgtt cccatgtggc      1260
agagtcagtg tgtcccaaac tagcaagctg acaagagcag aagccgtttt ccccgatgtg      1320
gactacgtga attccactga agccgaaacg atcctggaca atatcacaca gagcactcag      1380
tctttcaacg acttcacacg ggttgtggga ggagaggacg ccaaacccgg ccagtttcct      1440
tggcaagtcg ttcttaacgg caaggtcgac gccttttgtg agggagtat tgtgaacgag       1500 aaatggattg tcaccgctgc tcattgtgtt gaaactgggg tgaaaatcac tgttgtcgca      1560
ggagagcaca atatcgaaga acagaacac accgagcaga acgcaacgt tattcggatc        1620 attccacatc acaactacaa tgctgccatc aacaagtaca ccacgacat tgcgctgctg       1680 gagttggatg aacctctcgt gctcaactcc tatgtgaccc caatctgcat agcagataag      1740
gagtatacca acatcttcct gaagtttggg tcaggttatg tgtcaggctg ggacgagtg       1800 tttcataaag ggagatcagc actggtgttg cagtatctgc gcgtaccact ggtggatcgg      1860
gctacttgcc tgcgtagcac aaaattcacc atctacaaca acatgttttg tgccggtttt      1920
cacgaaggcg gcagggacag ctgtcaggga gattccggag ggcctcatgt cacagaggtc      1980
gagggcacct cctttctcac tgggattata agctggggag aagaatgcgc catgaaggg      2040 aagtacggca tatacacgaa agtgtctaga tacgtgaatt ggattaagga aaagaccaaa      2100
ctgacgtgag cggccgcggt accggatcag cctcgactgt gccttctagt tgccagccat      2160
ctgttgtttg cccctccccc gtgccttcct tgaccctgga aggtgccact cccactgtcc      2220
tttcctaata aaatgaggaa attgcatcgc attgtctgag taggtgtcat tctattctgg      2280
ggggtggggt ggggcaggac agcaagggg aggattggga agacaatagc aggcatgctg       2340
gggatgcggt gggctctatg gcttctgagg cggaaagaac cag                        2383
```

<210> SEQ ID NO 6
<211> LENGTH: 554
<212> TYPE: DNA
<213> ORGANISM: Artificial sequence
<220> FEATURE:
<223> OTHER INFORMATION: Nucleotide sequence of codon optimised exons 3 to 5 of FIX

<400> SEQUENCE: 6

```
tcgcaggaga gcacaatatc gaagagacag aacacaccga gcagaaacgc aacgttattc      60
ggatcattcc acatcacaac tacaatgctg ccatcaacaa gtacaaccac gacattgcgc      120
tgctggagtt ggatgaacct ctcgtgctca actcctatgt gaccccaatc tgcatagcag      180
ataaggagta taccaacatc ttcctgaagt ttgggtcagg ttatgtgtca ggctggggac      240
gagtgtttca taagggaga tcagcactgg tgttgcagta tctgcgcgta ccactggtgg       300
atcgggctac ttgcctgcgt agcacaaaat tcaccatcta caacaacatg ttttgtgccg      360
gttttcacga aggcggcagg gacagctgtc agggagattc cggagggcct catgtcacag      420
aggtcgaggg cacctccttt ctcactggga ttataagctg gggagaagaa tgcgccatga      480
aagggaagta cggcatatac acgaaagtgt ctagatacgt gaattggatt aaggaaaaga      540
ccaaactgac gtga                                                        554
```

FACTOR IX GENE THERAPY

CROSS-REFERENCE TO RELATED APPLICATIONS

This application is a continuation of U.S. patent application Ser. No. 15/525,836, filed May 10, 2017, which is a national phase entry under 35 U.S.C. § 371 of International Patent Application PCT/GB2015/053438, filed Nov. 12, 2015, designating the United States of America and published in English as International Patent Publication WO/2016/075473 on May 19, 2016, which claims the benefit under Article 8 of the Patent Cooperation Treaty to United Kingdom Patent Application Serial No. 1420139.6, filed Nov. 12, 2014, the entirety of each of which are incorporated herein by this reference.

TECHNICAL FIELD

The invention relates to a new more potent coagulation factor IX (FIX) expression cassette for gene therapy of haemophilia B (HB).

STATEMENT ACCORDING TO 37 C.F.R. § 1.821(c) or (e)—SEQUENCE LISTING SUBMITTED AS A TXT FILE

Pursuant to 37 C.F.R. § 1.821(c) or (e), files containing a TXT version of the Sequence Listing have been submitted concomitant with this application, the contents of which are hereby incorporated by reference.

BACKGROUND

Haemophilia B, an X-linked life threatening bleeding disorder affects 1:30,000 males. Current treatment involves frequent intravenous injections (2-3 times per week) of FIX protein. This treatment is highly effective at arresting bleeding but it is not curative and is extremely expensive (£150,000/patient/year), thus making it unaffordable by the majority of haemophilia B patients in the World. Gene therapy for HB offers the potential for a cure through persistent, endogenous production of FIX following the transfer of a normal copy of the FIX gene to an affected patient. Even a small rise in circulating FIX to ≥1% of normal levels can significantly ameliorate the severe bleeding phenotype.

The inventors have recently successfully piloted a gene therapy approach using adeno-associated viral vectors (AAV) to mediate transfer and expression of the gene for normal coagulation factor IX (FIX) in the liver. Preliminary results of this successful academic, investigator led, trial were published in the New England Journal of Medicine, with experts in the field lauding the work, and calling it a "landmark study".

BRIEF SUMMARY

Despite the initial success, some obstacles remain to the overriding goal of making AAV-mediated transfer of the normal FIX gene the world-wide curative standard-of-care. Foremost among these is the body's immune response to cells that have been transduced with the viral vector that resulted in asymptomatic, transient elevation of serum liver enzymes, suggesting local inflammation in the liver. Treatment with a short course of steroids led to rapid normalisation of the liver enzymes and continued expression of FIX, but at levels below those that had been generated before the episodes of liver inflammation. Since this observation only occurred at the high dose level, current efforts are focused on improving the potency and transduction efficiency of AAV vectors so that therapeutic gene transfer can be achieved with lower, potentially safer vector doses. To this end, the inventors have developed a new AAV expression cassette, referred to as HLP2-TI-codop-FIX, which mediates transgene expression at levels that are up to four fold higher than previously observed with the self-complementary (sc) LP1-hFIXco cassette used in the previous clinical trial. HLP2-TI-codop-FIX improves the safety profile of AAV mediated gene transfer whilst reducing the burden on vector production.

Figure 2:
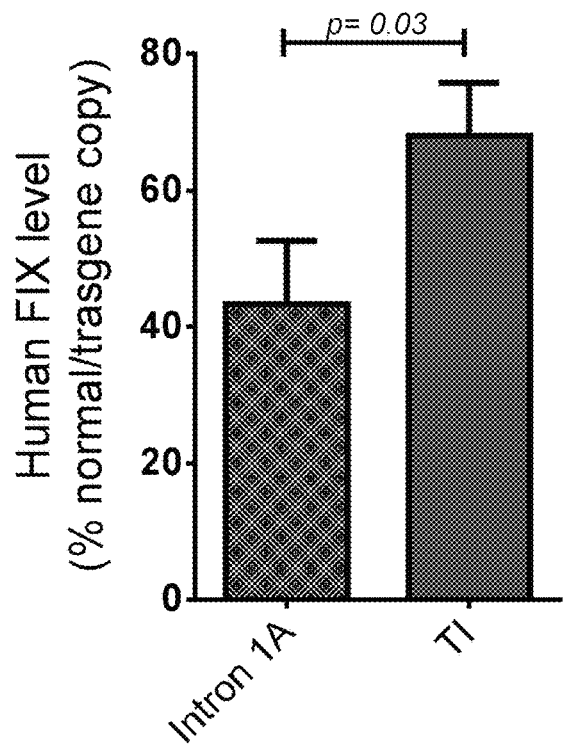

The aspects of HLP2-TI-codop-FIX which make it different from previously used vectors include the following:

1. It is a single stranded vector. This allows a larger transgene to be packaged in the AAV than with self-complementary AAV;

2. A new synthetic liver promoter (HLP2). This promoter is a modified promoter which contains an extra enhancer region to increase expression;

3. Truncated 299 bp intron (TI) derived by engineering sequences from wild type FIX intron 1A which spans 6.2kb. The truncated intron (TI) in this expression cassette is placed in its native position between exon 1 and exon 2 of the FIX. Despite its smaller size, it increases expression levels by 1.6 fold over that observed with wild type full length intron 1A; and 4. New codon optimised FIX to increase expression over wild-type sequence by almost two fold (FIG. 2).

In a first aspect of the invention, there is provided a vector for expressing factor IX protein, the vector comprising a promoter, a nucleotide sequence encoding for a functional factor IX protein and an intron sequence, wherein the intron sequence is positioned between exon 1 and exon 2 of the nucleotide sequence encoding for a functional factor IX protein, and wherein the intron sequence has at least 80% identity to the sequence of SEQ ID NO. 1.

The intron sequence in the vector is derived from intron 1A of the wild type FIX gene. It has been found that truncating the sequence of intron 1A causes expression of the vector to be increased. It is thought that the truncation of intron 1A may delete a repressor element in the intron.

Truncation of the intron 1A sequence also results in the nucleotide sequence of the vector being shorter which allows more efficient packaging of the vector in a viral delivery system.

In the vector of the invention, the intron sequence is positioned between exon 1 and exon 2 of the nucleotide sequence encoding for a functional factor IX protein. The complete sequence of the human FIX gene is well known, including the sequences of the introns and exons. For example, this information can be found on Genbank (http://www.ncbi.nlm.nih.gov/genbank) under accession numbers J00137.1; BC109215.1; BC109214.1; AB186358.1; and FR846239.1. Therefore, it is well within the abilities of a skilled person to determine where in the FIX coding sequence the intron sequence is located and in particular, between exon 1 and 2 of the FIX gene. Generally, when protein coding sequences are incorporated into vectors, the coding sequence does not contain any introns.

The intron sequence has at least 80% identity to the sequence of SEQ ID NO. 1. In some embodiments, the intron sequence has at least 82% identity to the sequence of SEQ ID NO. 1. In other embodiments, the intron sequence has at least 84% identity to the sequence of SEQ ID NO. 1. In particular embodiments, the intron sequence has at least 86% identity to the sequence of SEQ ID NO. 1. In further embodiments, the intron sequence has at least 88% identity to the sequence of SEQ ID NO. 1. In some embodiments, the intron sequence has at least 90% identity to the sequence of SEQ ID NO. 1. In other embodiments, the intron sequence has at least 91% identity to the sequence of SEQ ID NO. 1. In particular embodiments, the intron sequence has at least 92% identity to the sequence of SEQ ID NO. 1. In further embodiments, the intron sequence has at least 93% identity to the sequence of SEQ ID NO. 1. In some embodiments, the intron sequence has at least 94% identity to the sequence of SEQ ID NO. 1. In other embodiments, the intron sequence has at least 95% identity to the sequence of SEQ ID NO. 1. In particular embodiments, the intron sequence has at least 96% identity to the sequence of SEQ ID NO. 1. In further embodiments, the intron sequence has at least 97% identity to the sequence of SEQ ID NO. 1. In some embodiments, the intron sequence has at least 98% identity to the sequence of SEQ ID NO. 1. In other embodiments, the intron sequence has at least 99% identity to the sequence of SEQ ID NO. 1. In particular embodiments, the intron sequence has the sequence of SEQ ID NO. 1.

The truncated intron sequence is preferably between 270 and 330 nucleotides in length. In some embodiments, the intron sequence is between 280 and 320 nucleotides in length. In other embodiments, the intron sequence is between 290 and 310 nucleotides in length. In particular embodiments, the intron sequence is between 295 and 305 nucleotides in length. In specific embodiments, the intron sequence is between 295 and 300 nucleotides in length.

The vector contains a nucleotide sequence encoding for a functional factor IX protein so that when this sequence is expressed, a functional FIX protein is produced by the cell in which the vector is contained. When expressed in a subject, e.g. a human patient, the functional FIX protein is one which can take part in the coagulation cascade to allow blood clotting to take place. This causes a decrease in the time it takes for blood to clot in a subject suffering from haemophilia B. The functional FIX protein can be activated to produce the enzymatically active factor IXa which can convert factor X to factor Xa.

The sequence of the FIX protein produced by expression of the vector may be the wild type FIX sequence. In one embodiment, the nucleotide sequence encoding for a functional factor IX protein consists of exons 1 to 5 of the FIX gene. The FIX gene normally contains 8 exons, with exons 6 to 8 encoding an untranslated region. The advantage of using a shorter sequence is that it can be incorporated into a vector more easily and more effectively.

As mentioned above, the sequence of the FIX gene is well known to a skilled person and therefore, it would be well within the capabilities of a skilled person to produce a nucleotide sequence encoding for a functional factor IX protein.

The nucleotide sequence encoding for a functional FIX protein preferably has at least 80% identity to the sequence of SEQ ID NO. 2. In some embodiments, the nucleotide sequence has at least 82% identity to the sequence of SEQ ID NO. 2. In other embodiments, the nucleotide sequence has at least 84% identity to the sequence of SEQ ID NO. 2. In further embodiments, the nucleotide sequence has at least 86% identity to the sequence of SEQ ID NO. 2. In particular embodiments, the nucleotide sequence has at least 88% identity to the sequence of SEQ ID NO. 2. In some embodiments, the nucleotide sequence has at least 90% identity to the sequence of SEQ ID NO. 2. In other embodiments, the nucleotide sequence has at least 91% identity to the sequence of SEQ ID NO. 2. In further embodiments, the nucleotide sequence has at least 92% identity to the sequence of SEQ ID NO. 2. In particular embodiments, the nucleotide sequence has at least 93% identity to the sequence of SEQ ID NO. 2. In some embodiments, the nucleotide sequence has at least 94% identity to the sequence of SEQ ID NO. 2. In other embodiments, the nucleotide sequence has at least 95% identity to the sequence of SEQ ID NO. 2. In further embodiments, the nucleotide sequence has at least 96% identity to the sequence of SEQ ID NO. 2. In particular embodiments, the nucleotide sequence has at least 97% identity to the sequence of SEQ ID NO. 2. In some embodiments, the nucleotide sequence has at least 98% identity to the sequence of SEQ ID NO. 2. In other embodiments, the nucleotide sequence has at least 99% identity to the sequence of SEQ ID NO. 2. In preferred embodiments, the nucleotide sequence has the sequence of SEQ ID NO. 2.

When the nucleotide sequence encoding for a functional FIX protein has sequence identity to the sequence of SEQ ID NO. 2, this does not include the intron sequence which is positioned between exon 1 and exon 2 of the nucleotide sequence encoding for a functional factor IX protein. For example, when the nucleotide sequence encoding for a functional FIX protein has the sequence of SEQ ID NO. 2 and the intron sequence has the sequence of SEQ ID NO. 1, in the nucleotide sequence of the actual vector, the sequence of SEQ ID NO. 1 will appear within SEQ ID NO. 2. This means that there will be a portion of SEQ ID NO. 2 followed by SEQ ID NO. 1 followed by the remaining portion of SEQ ID NO. 2.

The sequence of SEQ ID NO. 2 is a codon optimised FIX nucleotide sequence in which the sequence of exons 3 to 5 has been codon optimised. The sequence of exons 1 and 2 of SEQ ID NO. 2 is the wild type FIX sequence. The sequence of exons 3 to 5 has not been codon optimised in a normal way. Instead, the codons have been selected based on the codons used for proteins which are expressed at a high level in the liver. The reason for this is that the vector is normally expressed in the liver. This special codon optimisation process has been found to produce a nucleotide sequence which gives surprisingly high expression. The wild type sequence has been used for exons 1 and 2 to help to ensure that splicing is not affected when the intron is removed during processing of the RNA molecule expressed from the nucleotide sequence.

As described above, the vector comprises a nucleotide sequence encoding for a functional factor IX protein and an intron sequence, wherein the intron sequence is positioned between exon 1 and exon 2 of the nucleotide sequence encoding for a functional factor IX protein, and wherein the intron sequence has at least 80% identity to the sequence of SEQ ID NO. 1. In various embodiments, exons 3 to 5 of the nucleotide sequence encoding for a functional factor IX protein has 80% identity to the sequence of SEQ ID NO. 6. In some embodiments, the nucleotide sequence of exons 3 to 5 has at least 82% identity to the sequence of SEQ ID NO. 6. In other embodiments, the nucleotide sequence of exons 3 to 5 has at least 84% identity to the sequence of SEQ ID NO. 6. In further embodiments, the nucleotide sequence of exons 3 to 5 has at least 86% identity to the sequence of SEQ ID NO. 6. In particular embodiments, the nucleotide sequence of exons 3 to 5 has at least 88% identity to the sequence of SEQ ID NO. 6. In some embodiments, the nucleotide sequence of exons 3 to 5 has at least 90% identity to the sequence of SEQ ID NO. 6. In other embodiments, the nucleotide sequence of exons 3 to 5 has at least 91% identity to the sequence of SEQ ID NO. 6. In further embodiments, the nucleotide sequence of exons 3 to 5 has at least 92% identity to the sequence of SEQ ID NO. 6. In particular embodiments, the nucleotide sequence of exons 3 to 5 has at least 93% identity to the sequence of SEQ ID NO. 6. In some embodiments, the nucleotide sequence of exons 3 to 5 has at least 94% identity to the sequence of SEQ ID NO. 6. In other embodiments, the nucleotide sequence of exons 3 to 5 has at least 95% identity to the sequence of SEQ ID NO. 6. In further embodiments, the nucleotide sequence of exons 3 to 5 has at least 96% identity to the sequence of SEQ ID NO. 6. In particular embodiments, the nucleotide sequence of exons 3 to 5 has at least 97% identity to the sequence of SEQ ID NO. 6. In some embodiments, the nucleotide sequence of exons 3 to 5 has at least 98% identity to the sequence of SEQ ID NO. 6. In other embodiments, the nucleotide sequence of exons 3 to 5 has at least 99% identity to the sequence of SEQ ID NO. 6. In preferred embodiments, the nucleotide sequence of exons 3 to 5 has the sequence of SEQ ID NO. 6.

The nucleotide sequence encoding for a functional FIX protein is preferably between 1335 and 1435 nucleotides in length. In some embodiments, the nucleotide sequence encoding for a functional FIX protein is between 1360 and 1410 nucleotides in length. In other embodiments, the nucleotide sequence encoding for a functional FIX protein is between 1375 and 1395 nucleotides in length. In particular embodiments, the nucleotide sequence encoding for a functional FIX protein is between 1380 and 1390 nucleotides in length.

In some embodiments, the nucleotide sequence encoding for a functional FIX protein, including the intron sequence between exons 1 and 2, has 80% identity to the sequence of SEQ ID NO. 3. In some embodiments, the nucleotide sequence has at least 82% identity to the sequence of SEQ ID NO. 3. In other embodiments, the nucleotide sequence has at least 84% identity to the sequence of SEQ ID NO. 3. In further embodiments, the nucleotide sequence has at least 86% identity to the sequence of SEQ ID NO. 3. In particular embodiments, the nucleotide sequence has at least 88% identity to the sequence of SEQ ID NO. 3. In some embodiments, the nucleotide sequence has at least 90% identity to the sequence of SEQ ID NO. 3. In other embodiments, the nucleotide sequence has at least 91% identity to the sequence of SEQ ID NO. 3. In further embodiments, the nucleotide sequence has at least 92% identity to the sequence of SEQ ID NO. 3. In particular embodiments, the nucleotide sequence has at least 93% identity to the sequence of SEQ ID NO. 3. In some embodiments, the nucleotide sequence has at least 94% identity to the sequence of SEQ ID NO. 3. In other embodiments, the nucleotide sequence has at least 95% identity to the sequence of SEQ ID NO. 3. In further embodiments, the nucleotide sequence has at least 96% identity to the sequence of SEQ ID NO. 3. In particular embodiments, the nucleotide sequence has at least 97% identity to the sequence of SEQ ID NO. 3. In some embodiments, the nucleotide sequence has at least 98% identity to the sequence of SEQ ID NO. 3. In other embodiments, the nucleotide sequence has at least 99% identity to the sequence of SEQ ID NO. 3. In preferred embodiments, the nucleotide sequence encoding for a functional FIX protein, including the intron sequence between exons 1 and 2, has the sequence of SEQ ID NO. 3.

Therefore, in preferred embodiments, the present invention provides a vector for expressing factor IX protein, the vector comprising a promoter, and a nucleotide sequence encoding for a functional factor IX protein, wherein an intron sequence is positioned between exon 1 and exon 2 of the nucleotide sequence encoding for a functional factor IX protein, and wherein the factor IX nucleotide sequence, including the intron sequence, has at least 80% identity to the sequence of SEQ ID NO. 3. As described above, the percentage identity may be higher.

The promoter causes expression of the nucleotide sequence encoding for a functional factor IX protein. Any appropriate promoter may be used, such as HLP, LP1, HCR-hAAT, ApoE-hAAT, and LSP. These promoters are described in more detail in the following references: HLP: McIntosh J. et al., Blood 2013 Apr. 25, 121(17):3335-44; LP1: Nathwani et al., Blood. 2006 Apr. 1, 107(7): 2653-2661; HCR-hAAT: Miao et al., Mol Ther. 2000; 1: 522-532; ApoE-hAAT: Okuyama et al., Human Gene Therapy, 7, 637-645 (1996); and LSP: Wang et al., Proc Natl Acad Sci USA. 1999 Mar. 30, 96(7): 3906-3910. A preferred promoter is also described in WO 2011/005968. Preferably, the promoter is a liver specific promoter.

The promoter preferably has a nucleotide sequence which has at least 80% identity to the sequence of SEQ ID NO. 4. In some embodiments, the nucleotide sequence has at least 82% identity to the sequence of SEQ ID NO. 4. In other embodiments, the nucleotide sequence has at least 84% identity to the sequence of SEQ ID NO. 4. In further embodiments, the nucleotide sequence has at least 86% identity to the sequence of SEQ ID NO. 4. In particular embodiments, the nucleotide sequence has at least 88% identity to the sequence of SEQ ID NO. 4. In some embodiments, the nucleotide sequence has at least 90% identity to the sequence of SEQ ID NO. 4. In other embodiments, the nucleotide sequence has at least 91% identity to the sequence of SEQ ID NO. 4. In further embodiments, the nucleotide sequence has at least 92% identity to the sequence of SEQ ID NO. 4. In particular embodiments, the nucleotide sequence has at least 93% identity to the sequence of SEQ ID NO. 4. In some embodiments, the nucleotide sequence has at least 94% identity to the sequence of SEQ ID NO. 4. In other embodiments, the nucleotide sequence has at least 95% identity to the sequence of SEQ ID NO. 4. In further embodiments, the nucleotide sequence has at least 96% identity to the sequence of SEQ ID NO. 4. In particular embodiments, the nucleotide sequence has at least 97% identity to the sequence of SEQ ID NO. 4. In some embodiments, the nucleotide sequence has at least 98% identity to the sequence of SEQ ID NO. 4. In other embodiments, the nucleotide sequence has at least 99% identity to the sequence of SEQ ID NO. 4. In preferred embodiments, the nucleotide sequence of the promoter is the sequence of SEQ ID NO. 4.

The promoter having SEQ ID NO. 4 is a liver specific promoter which has been found to give particularly good expression in the liver. Whilst giving good expression, this promoter is also relatively small which allows more efficient packaging of the vector.

The nucleotide sequence of the promoter is preferably between 300 and 400 nucleotides in length. In some embodiments, the nucleotide sequence of the promoter is between 330 and 380 nucleotides in length. In other embodiments, the nucleotide sequence of the promoter is between 345 and 365 nucleotides in length. In particular embodiments, the nucleotide sequence of the promoter is between 350 and 360 nucleotides in length.

The vector may be any appropriate vector for expressing the FIX protein, including viral and non-viral vectors. Viral vectors include a parvovirus, an adenovirus, a retrovirus, a lentivirus or a herpes simplex virus. The parvovirus may be an adenovirus-associated virus (AAV). The vector is preferably a recombinant adeno-associated viral (rAAV) vector or a lentiviral vector. More preferably, the vector is an rAAV vector.

A vector according to the invention may be a gene delivery vector. Such a gene delivery vector may be a viral gene delivery vector or a non-viral gene delivery vector.

Accordingly, the present invention provides gene delivery vectors based on animal parvoviruses, in particular dependoviruses such as infectious human or simian AAV, and the components thereof (e.g., an animal parvovirus genome) for use as vectors for introduction and/or expression of a factor IX protein in a mammalian cell. The term "parvoviral" as used herein thus encompasses dependoviruses such as any type of AAV.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is, however, understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

In an AAV suitable for use as a gene therapy vector, the vector genome typically comprises a nucleic acid to be packaged for delivery to a target cell. According to this particular embodiment, the heterologous nucleotide sequence is located between the viral ITRs at either end of the vector genome. In further preferred embodiments, the parvovirus (e.g. AAV) cap genes and parvovirus (e.g. AAV) rep genes are deleted from the template genome (and thus from the virion DNA produced therefrom). This configuration maximizes the size of the nucleic acid sequence(s) that can be carried by the parvovirus capsid.

According to this particular embodiment, the nucleic acid is located between the viral ITRs at either end of the substrate. It is possible for a parvoviral genome to function with only one ITR. Thus, in a gene therapy vector of the invention based on a parvovirus, the vector genome is flanked by at least one ITR, but, more typically, by two AAV ITRs (generally with one either side of the vector genome, i.e. one at the 5' end and one at the 3' end). There may be intervening sequences between the nucleic acid in the vector genome and one or more of the ITRs.

Preferably, the nucleotide sequence encoding a functional factor IX protein (for expression in the mammalian cell) will be incorporated into a parvoviral genome located between two regular ITRs or located on either side of an ITR engineered with two D regions.

AAV sequences that may be used in the present invention for the production of AAV gene therapy vectors can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini et al, 1997; Srivastava et al, 1983; Chiorini et al, 1999; Rutledge et al, 1998; and Wu et al, 2000. AAV serotype 1, 2, 3, 4, 5, 6, 7, 8 or 9 may be used in the present invention. However, AAV serotypes 1, 5 or 8 are preferred sources of AAV sequences for use in the context of the present invention. The sequences from the AAV serotypes may be mutated or engineered when being used in the production of gene therapy vectors.

Preferably, the AAV ITR sequences for use in the context of the present invention are derived from AAV1, AAV2, AAV4 and/or AAV6. Likewise, the Rep (Rep78 and Rep52) coding sequences are preferably derived from AAV1, AAV2, AAV4 and/or AAV6. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al, 1999). Moreover, the Rep sequences and ITRs of many AAV serotypes are known to efficiently cross-complement (i.e., functionally substitute) corresponding sequences from other serotypes in production of AAV particles in mammalian cells. US 2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped AAV particles comprising the capsid proteins of a serotype (e.g., AAV1, 5 or 8) and the Rep and/or ITR sequences of another AAV serotype (e.g., AAV2). Such pseudotyped rAAV particles are a part of the present invention.

Modified "AAV" sequences also can be used in the context of the present invention, e.g. for the production of AAV gene therapy vectors. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV5 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of AAV5 or pseudotyped AAV5 vectors. For example, the start codon of the Rep sequences can be modified, VP splice sites can be modified or eliminated, and/or the VP1 start codon and nearby nucleotides can be modified to improve the production of AAV5 vectors.

Thus, the viral capsid used in the invention may be from any parvovirus, either an autonomous parvovirus or dependovirus, as described above. Preferably, the viral capsid is an AAV capsid (e. g., AAV1, AAV2, AAV3, AAV4, AAV5 or AAV6 capsid). In general, the AAV1 capsid or AAV6 capsid are preferred. The choice of parvovirus capsid may be based on a number of considerations as known in the art, e.g., the target cell type, the desired level of expression, the nature of the heterologous nucleotide sequence to be expressed, issues related to viral production, and the like. For example, the AAV1 and AAV6 capsid may be advantageously employed for skeletal muscle; AAV1, AAV5 and AAV8 for the liver and cells of the central nervous system (e.g., brain); AAV5 for cells in the airway and lung or brain; AAV3 for bone marrow cells; and AAV4 for particular cells in the brain (e. g., appendable cells).

It is within the technical skills of the skilled person to select the most appropriate virus, virus subtype or virus serotype. Some subtypes or serotypes may be more appropriate than others for a certain type of tissue.

For example, liver-specific expression of a nucleic acid of the invention may advantageously be induced by AAV-mediated transduction of liver cells. Liver is amenable to AAV-mediated transduction, and different serotypes may be used (for example, AAV1, AAV5 or AAV8). Transduction of muscle may be accomplished by administration of an AAV encoding a nucleic acid via the blood stream. Thus, intravenous or intra-arterial administration is applicable.

A parvovirus gene therapy vector prepared according to the invention may be a "hybrid" particle in which the viral ITRs and viral capsid are from different parvoviruses. Preferably, the viral TRs and capsid are from different serotypes of AAV. Likewise, the parvovirus may have a "chimeric" capsid (e. g., containing sequences from different parvoviruses, preferably different AAV serotypes) or a "targeted" capsid (e. g., a directed tropism).

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans-acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. A parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a parvoviral (AAV) vector that is unable to further propagate after initial introduction into a cell. Such a safety mechanism for limiting undesirable vector propagation in a recipient may be provided by using AAV with a chimeric ITR as described in US 2003148506.

Those skilled in the art will appreciate that the viral Rep protein(s) used for producing an AAV vector of the invention may be selected with consideration for the source of the viral ITRs. For example, the AAV5 ITR typically interacts more efficiently with the AAV5 Rep protein, although it is not necessary that the serotype of ITR and Rep protein(s) are matched.

The ITR(s) used in the invention are typically functional, i.e. they may be fully resolvable and are preferably AAV sequences, with serotypes 1, 2, 3, 4, 5 or 6 being preferred. Resolvable AAV ITRs according to the present invention need not have a wild-type ITR sequence (e. g., a wild-type sequence may be altered by insertion, deletion, truncation or missense mutations), as long as the ITR mediates the desired functions, e. g., virus packaging, integration, and/or provirus rescue, and the like.

Advantageously, by using a gene therapy vector as compared with previous approaches, the restoration of protein synthesis, i.e. factor IX synthesis, is a characteristic that the transduced cells acquire permanently or for a sustained period of time, thus avoiding the need for continuous administration to achieve a therapeutic effect.

Accordingly, the vectors of the invention therefore represent a tool for the development of strategies for the in vivo delivery of a FIX nucleotide sequence, by engineering the nucleic acid within a gene therapy vector that efficiently transduces an appropriate cell type, such as a liver cell.

Preferably, the vector is a single stranded vector rather than a self-complementary vector. Surprisingly, this has been shown to give better protein expression.

The vector may further comprise a poly A tail. Preferably, this is positioned downstream of the nucleotide sequence encoding for a functional FIX protein. Preferably, the poly A tail is a bovine growth hormone poly A tail (bGHpA). Preferably, this is between 250 and 270 nucleotides in length.

In a preferred embodiment, the vector comprises a nucleotide sequence which has 80% identity to the sequence of SEQ ID NO. 5. In some embodiments, the nucleotide sequence has at least 82% identity to the sequence of SEQ ID NO. 5. In other embodiments, the nucleotide sequence has at least 84% identity to the sequence of SEQ ID NO. 5. In further embodiments, the nucleotide sequence has at least 86% identity to the sequence of SEQ ID NO. 5. In particular embodiments, the nucleotide sequence has at least 88% identity to the sequence of SEQ ID NO. 5. In some embodiments, the nucleotide sequence has at least 90% identity to the sequence of SEQ ID NO. 5. In other embodiments, the nucleotide sequence has at least 91% identity to the sequence of SEQ ID NO. 5. In further embodiments, the nucleotide sequence has at least 92% identity to the sequence of SEQ ID NO. 5. In particular embodiments, the nucleotide sequence has at least 93% identity to the sequence of SEQ ID NO. 5. In some embodiments, the nucleotide sequence has at least 94% identity to the sequence of SEQ ID NO. 5. In other embodiments, the nucleotide sequence has at least 95% identity to the sequence of SEQ ID NO. 5. In further embodiments, the nucleotide sequence has at least 96% identity to the sequence of SEQ ID NO. 5. In particular embodiments, the nucleotide sequence has at least 97% identity to the sequence of SEQ ID NO. 5. In some embodiments, the nucleotide sequence has at least 98% identity to the sequence of SEQ ID NO. 5. In other embodiments, the nucleotide sequence has at least 99% identity to the sequence of SEQ ID NO. 5. In preferred embodiments, the vector comprises the nucleotide sequence of SEQ ID NO. 5.

In another aspect of the invention, there is provided a nucleic acid molecule comprising a nucleotide sequence encoding for a functional factor IX protein, wherein exons 3 to 5 of the nucleotide sequence have at least 80% identity to the sequence of SEQ ID NO. 6.

The invention also provides a vector comprising a nucleotide sequence encoding for a functional factor IX protein, wherein exons 3 to 5 of the nucleotide sequence have at least 80% identity to the sequence of SEQ ID NO. 6. The vector will comprise other elements to allow the functional FIX protein to be expressed such as a promoter. Such elements are well known to a person skilled in the art.

Additional features relating to the nucleotide sequence encoding for a functional factor IX protein, and exons 3 to 5 of the sequence, are described above.

In another aspect of the invention, there is provided a nucleic acid molecule comprising a nucleotide sequence encoding for a functional factor IX protein, the nucleotide sequence having at least 80% identity to the sequence of SEQ ID NO. 2.

The invention also provides a vector comprising a nucleotide sequence encoding for a functional factor IX protein, the nucleotide sequence having at least 80% identity to the sequence of SEQ ID NO. 2. The vector will comprise other elements to allow the functional FIX protein to be expressed such as a promoter. Such elements are well known to a person skilled in the art.

Additional features relating to the nucleotide sequence encoding for a functional factor IX protein are described above.

In another aspect of the invention, there is provided a nucleic acid molecule comprising a nucleotide sequence encoding for a functional factor IX protein and containing an intron sequence positioned between exon 1 and exon 2 of the factor IX sequence, wherein the nucleotide sequence has at least 80% identity to the sequence of SEQ ID NO. 3.

Additional features relating to the nucleotide sequence encoding for a functional factor IX protein and which contains an intron sequence are described above.

In another aspect of the invention, there is provided a nucleic acid molecule comprising an intron sequence having at least 80% identity to the sequence of SEQ ID NO. 1.

Additional features relating to the intron sequence are described above.

In another aspect of the invention, there is provided a nucleic acid molecule comprising a promoter, wherein the promoter has a nucleotide sequence having at least 80% identity to the sequence of SEQ ID NO. 4.

Additional features relating to the promoter sequence are described above.

Preferably, the nucleic acids described above are isolated.

It would be well with the capabilities of a skilled person to produce the nucleic acid molecules described above. This could be done, for example, using chemical synthesis of a given sequence.

Further, a skilled person would readily be able to determine whether a nucleic acid expresses a functional protein. Suitable methods would be apparent to those skilled in the art. For example, one suitable in vitro method involves inserting the nucleic acid into a vector, such as a lentiviral or an AAV vector, transducing host cells, such as 293T or HeLa cells, with the vector, and assaying for factor IX activity. Alternatively, a suitable in vivo method involves transducing a vector containing the nucleic acid into haemophiliac mice and assaying for functional factor IX in the plasma of the mice. Suitable methods are described in more detail below.

The nucleic acid can be any type of nucleic acid composed of nucleotides. The nucleic acid should be able to be expressed so that a protein is produced. Preferably, the nucleic acid is DNA or RNA.

The invention also provides a host cell comprising any one of the nucleic acid molecules or vectors described above. Preferably, the vector is capable of expressing the FIX nucleotide sequence in the host. The host may be any suitable host.

As used herein, the term "host" refers to organisms and/or cells which harbour a nucleic acid molecule or a vector of the invention, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host. A host cell may be in the form of a single cell, a population of similar or different cells, for example in the form of a culture (such as a liquid culture or a culture on a solid substrate), an organism or part thereof.

A host cell according to the invention may permit the expression of a nucleic acid molecule of the invention. Thus, the host cell may be, for example, a bacterial, a yeast, an insect or a mammalian cell.

In addition, the invention provides a transgenic animal comprising cells comprising the nucleic acid molecule encoding for a functional FIX protein described above or a vector described above. Preferably the animal is a non-human mammal, especially a primate. Alternatively, the animal may be a rodent, especially a mouse; or may be canine, feline, ovine or porcine.

In one aspect, the invention provides a pharmaceutical composition comprising a nucleic acid molecule or a vector of the invention and one or more pharmaceutically acceptable excipients. The one or more excipients include carriers, diluents and/or other medicinal agents, pharmaceutical agents or adjuvants, etc.

The invention also provides a method of treating haemophilia B comprising administering a therapeutically effective amount of a vector as described above to a patient suffering from haemophilia B. Preferably, the patient is human.

When haemophilia B is "treated" in the above method, this means that one or more symptoms of haemophilia are ameliorated. It does not mean that the symptoms of haemophilia are completely remedied so that they are no longer present in the patient, although in some methods, this may be the case. The method of treating results in one or more of the symptoms of haemophilia B being less severe than before treatment.

A "therapeutically effective amount" refers to an amount effective, at dosages and for periods of time necessary, to achieve the desired therapeutic result, such as raising the level of functional factor IX in a subject (so as to lead to functional factor IX production to a level sufficient to ameliorate the symptoms of haemophilia B).

Delivery of a nucleic acid or vector of the invention to a host cell in vivo may result in an increase of functional factor IX in the host, for example to a level that ameliorates one or more symptoms of haemophilia B.

The level of naturally occurring factor IX in a subject suffering from haemophilia B varies depending on the severity of the haemophilia. Patients with a severe form of the disease have factor IX levels of less than about 1% of the level found in a normal healthy subject (referred to herein as "a normal level"). It has been found that when the method of treatment of the invention is used, it can cause an increase in the level of functional factor IX to at least about 1% of normal levels. In a subject suffering from haemophilia B, an increase in circulating FIX to ≥1% of normal levels can significantly ameliorate the severe bleeding phenotype. In some embodiments, the method of treatment of the invention causes an increase in the level of functional factor IX to at least about 2%, at least about 3%, at least about 4%, at least about 10%, at least about 15%, at least about 20% or at least about 25% of normal levels. In a particular embodiment, the method of treatment of the invention causes an increase in the level of functional factor IX to at least about 30% of normal levels. This level of increase would virtually normalise coagulation of blood in subjects suffering haemophilia B. Such subjects are unlikely to require factor IX concentrates following trauma or during surgery.

In one embodiment, the method of treatment of the invention causes an increase in the level of functional factor IX to, at most, normal levels.

The level of functional factor IX can be measured relatively easily and methods for measuring factor IX levels are well known to those skilled in the art. Many clotting assays are available, including chromogenic and clotting based assays. ELISA tests are also widely available.

Further, the invention provides the nucleic acid molecule encoding for a functional FIX protein as described above or a vector as described above for use in therapy, for example, in the treatment of haemophilia B.

In addition, the invention provides the use of the nucleic acid molecule encoding for a functional FIX protein as described above or a vector as described above in the manufacture of a medicament for treating haemophilia B.

The invention also provided a method for delivery of a nucleotide sequence encoding a functional FIX protein to a subject, which method comprises administering to the said subject a nucleic acid molecule encoding a functional FIX protein as described above or a vector as described above.

In the description above, the term "identity" is used to refer to the similarity of two sequences. For the purpose of this invention, it is defined here that in order to determine the percent identity of two nucleotide sequences, the sequences are aligned for optimal comparison purposes (e.g., gaps can be introduced in the sequence of a first nucleic acid for optimal alignment with a second amino or nucleic acid sequence). The nucleotide residues at nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length. A sequence comparison is typically carried out over the entire length of the two sequences being compared.

The skilled person will be aware of the fact that several different computer programs are available to determine the homology or identity between two sequences. For instance, a comparison of sequences and determination of percent identity between two sequences can be accomplished using a mathematical algorithm. In a preferred embodiment, the percent identity between two nucleic acid sequences is determined using the sequence alignment software Clone Manager 9 (Sci-Ed software—www.scied.com) using global DNA alignment; parameters: both strands; scoring matrix: linear (mismatch 2, OpenGap 4, ExtGap 1).

Alternatively, the percent identity between two amino acid or nucleic acid sequences is determined using the Needleman and Wunsch (1970) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6.

The nucleic acid sequences of the present invention can further be used as a "query sequence" to perform a search against public databases to, for example, identify other family members or related sequences. Such searches can be performed using the BLASTN programs (version 2.0) of Altschul, et al, 1990. To obtain gapped alignments for comparison purposes, Gapped BLAST can be utilized as described in Altschul et al, 1997. When utilizing BLAST and Gapped BLAST programs, the default parameters of the respective programs (e.g. BLASTN) can be used. See the homepage of the National Center for Biotechnology Information at http://www.ncbi.nlm.nih.gov/.

All patent and literature references cited in the present specification are hereby incorporated by reference in their entirety.

A skilled person will appreciate that all aspects of the invention, whether they relate to, for example, the nucleic acid, the vector, the host cell or the use, are equally applicable to all other aspects of the invention. In particular, aspects of the method of treatment, for example, the administration of the nucleic acid or vector, may have been described in greater detail than in some of the other aspects of the invention, for example, relating to the use of the nucleic acid or vector for treating haemophilia B. However, the skilled person will appreciate where more detailed information has been given for a particular aspect of the invention, this information is generally equally applicable to other aspects of the invention. Further, the skilled person will also appreciate that the description relating to the method of treatment is equally applicable to the use of the nucleic acid or vector in treating haemophilia B.

DETAILED DESCRIPTION

The invention will now be described in detail by way of example only with reference to the figures in which:

FIG. 1 shows two vector constructs for delivering factor IX. The top construct HCR hAAT FIX is an existing factor IX gene expression vector used in a gene therapy trial. The bottom construct HCR hAAT FIX TI is the same except that it uses a truncated intron.

FIG. 2 shows FIX expression of the two constructs shown in FIG. 1 in mice following tail vein administration of an identical dose of vector. Expression levels for the HCR hAAT TI FIX vector were 1.8 fold higher than for the HCR hAAT FIX vector which was unexpected based on the prior art.

Figure 3:
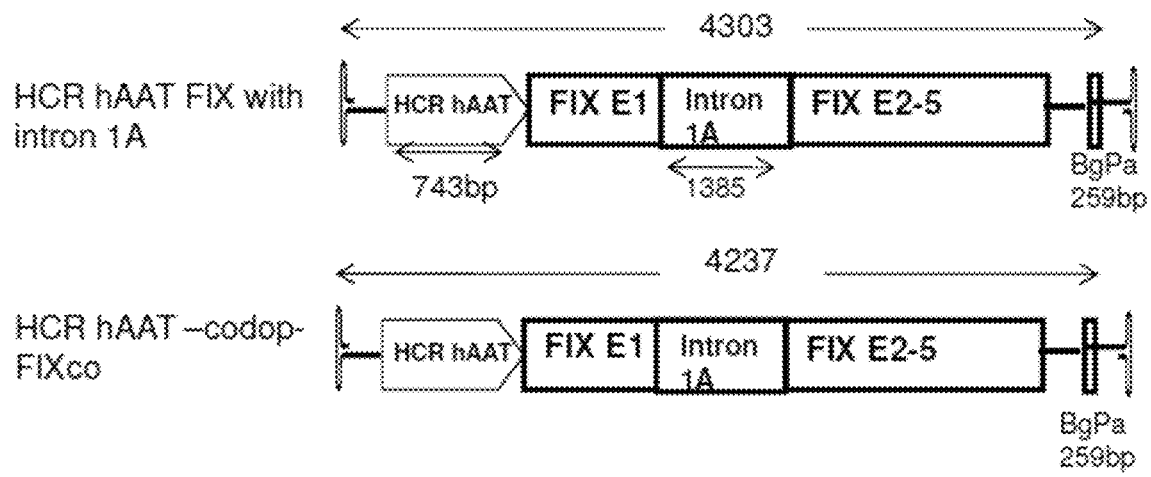

FIG. 3 shows two factor IX vector constructs. The top construct HCR-hAAT-FIX comprises the wild type factor IX sequence whereas the bottom construct HCR-hAAT-codop-FIX comprises a codon optimised factor IX sequence. In this sequence, exons 1 and 2 have the wild type sequence, whilst exons 3 to 5 have the codon optimised sequence.

Figure 4:
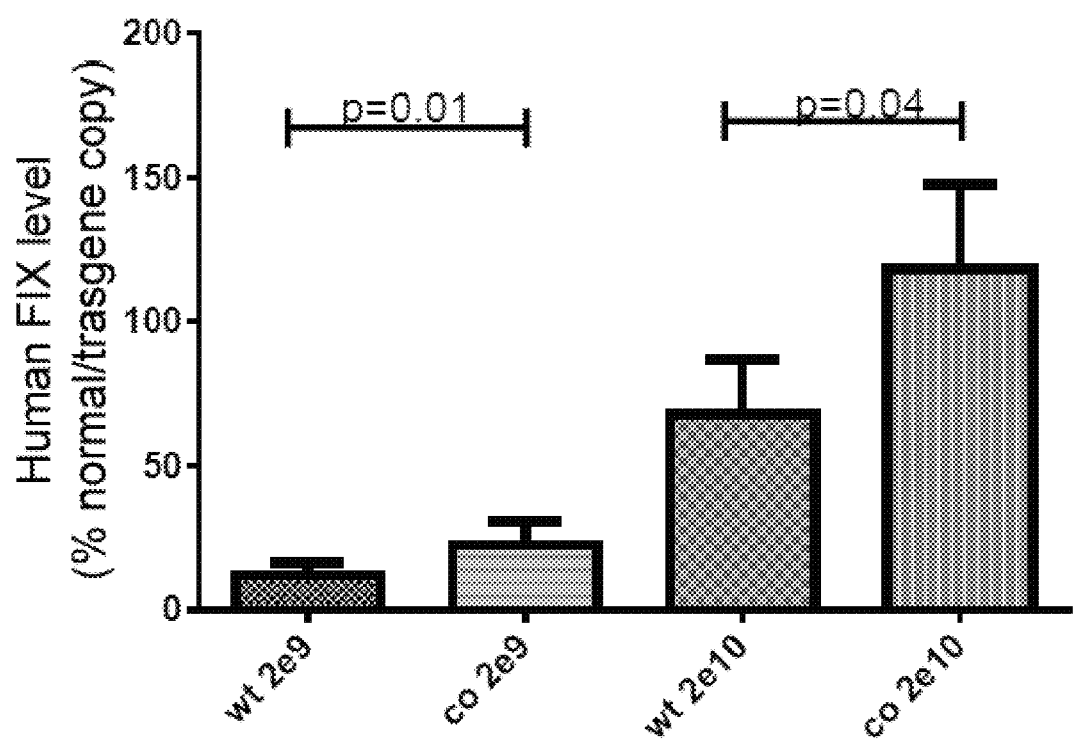

FIG. 4 shows FIX expression of the two constructs shown in FIG. 3 in mice following tail vein administration at two doses of vector. Expression levels for the HCR-hAAT-codop-FIX are significantly higher than for the HCR-hAAT-FIX vector.

Figure 5:
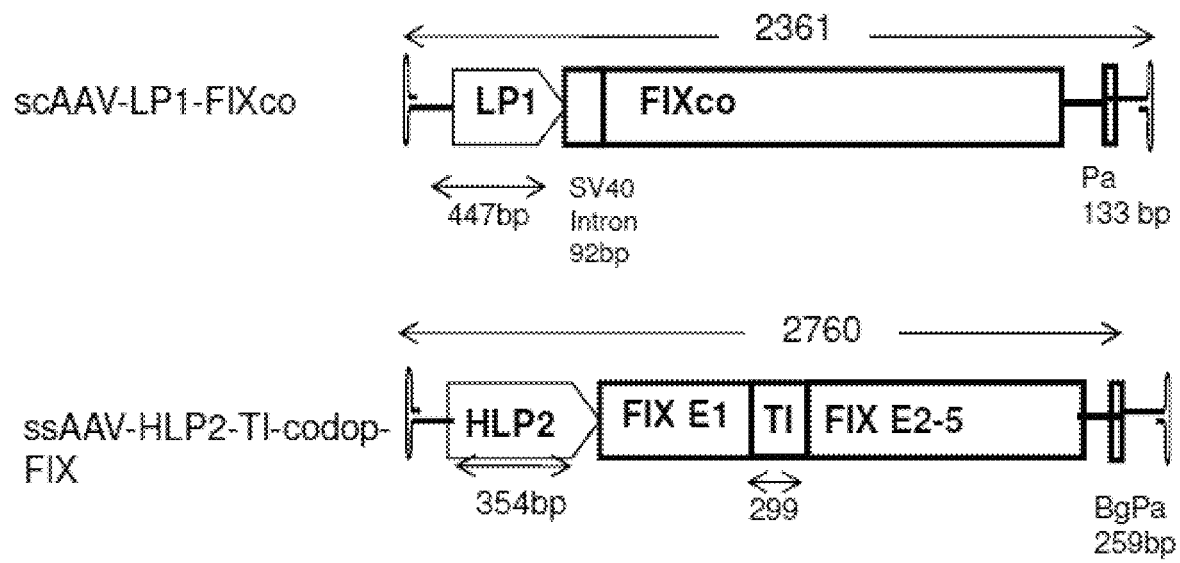

FIG. 5 shows two further vector constructs for delivering factor IX. The top construct scAAV-LP1-FIXco is a self-complementary vector being used in a haemophilia B clinical trial. The bottom construct scAAV-HLP2-TI-codop-FIX is a single stranded vector which uses a new liver specific promoter (HLP2). In this construct, exons 1 and 2 have the wild type sequence, whilst exons 3 to 5 have the codon optimised sequence.

Figure 6:
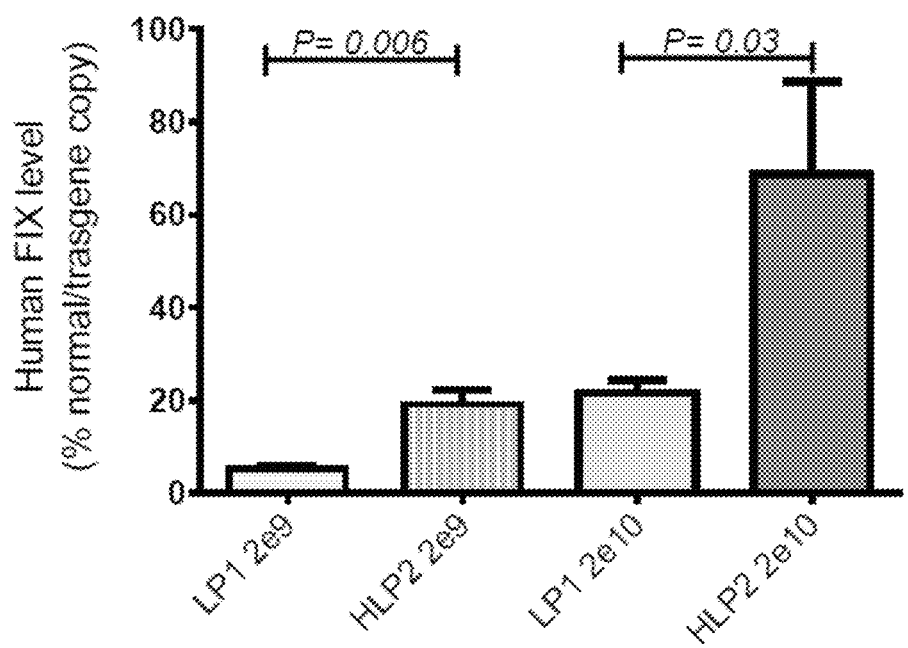

FIG. 6 shows FIX expression of the two constructs shown in FIG. 5 in mice following tail vein administration of an equivalent number of vector particles as assessed by a gel based titration method. AAV8 capsid pseudotyped single stranded HLP2-TI-codop-FIX mediated at least 3 fold higher levels of FIX when compared to scAAV-LP1-FIXco. This is surprising as self-complementary vectors have previously been shown to mediate substantially higher levels of expression than possible with single-stranded AAV-FIX constructs (Wu et al. Mol Ther. 2008 February; 16(2):280-9 and Nathwani et al. Blood. 2006 Apr. 1; 107(7):2653-61). However, these data show that when optimally configured with regards to inclusion of a strong promoter and efficient splice sites, a single stranded AAV can mediate higher levels of transgene expression than achievable with self-complementary AAV.

The overriding goal of the inventors' research program is to establish a cure for haemophilia B (HB) that is safe, effective and widely available. They established proof-of-concept in a pivotal clinical trial in which a single peripheral vein administration of a self-complementary (sc) adeno-associated viral vector (AAV) expressing a codon optimised FIX transgene (scAAV2/8-LP1-hFIXco) resulted in: (1) stable (>48 months) expression of FIX at 1-6% without long lasting toxicity; (2) discontinuation of prophylaxis in 4/7 participants; (3) reduction in annual bleeding rate of >90% for the 6 subjects in the high dose cohort; and (4) a cost saving so far of £1.5M from reduction in FIX concentrate usage (Nathwani A C et al. N Engl J Med. 365:2357-65, 2011). Obstacles remain to the overriding goal of making AAV-mediated transfer of the normal FIX gene the worldwide curative standard-of-care. Foremost is the body's immune response to cells that have been transduced with the viral vector, resulting in asymptomatic, transient elevation of serum liver enzymes, suggesting local inflammation in the liver. This adverse event only occurred at the high dose but was relatively common (n=4/6). The inventors' efforts have therefore focused on improving potency and transduction efficiency of AAV vectors to enable therapeutic gene transfer in humans with lower, potentially safer vector doses. In pursuit of this goal, the inventors have developed a new more potent FIX expression cassette called HLP2-TI-codop-FIX for AAV mediated gene therapy of haemophilia B.

An initial evaluation compared a single stranded HCR hAAT FIX construct containing a truncated intron 1 (HCR-hAAT-TI-FIX) to an identical construct (HCR-hAAT-FIX) currently being used in an on-going gene therapy trial in mice following tail vein administration of an identical dose of vector. In brief, a dose of 1e11vg was administered into the tail vein of 4-6 week old male C57Bl/6 mice (N=4-6 animals/group). The vector dose was assessed by a gel based titration method described previously (Fagone et al., Hum Gene Ther Methods. 2012 Feb. 23 (1):1-7). FIX levels were assessed using the previously described ELISA method at 4 weeks after gene transfer (Nathwani et al., Mol Ther. 2011 May 19. (5):876-85). A 1.8 fold higher level of FIX in the cohort transduced with HCR hAAT TI FIX was observed per copy of the AAV-FIX transgene (as assessed by a PCR quantification method using primers to hAAT) in the liver at 4 weeks, which was unexpected based on prior art (FIG. 1).

The DNA sequences in HCR-hAAT-FIX were further modified using our in-house codon-optimization algorithm in which codons in the FIX cDNA for a given amino-acid were substituted with the codon most frequently used by the human albumin gene for the same amino-acid since the human albumin is expressed in abundance by the liver. The resulting codop-FIX cDNA was 85% identical to that previously used by our group scAAV-LP1-FIXco (Nathwani et al., Blood. 2006 Apr. 1. 107(7):2653-61). The codop-FIX cDNA was synthesized and cloned downstream of the HCR-hAAT promoter (FIG. 3). To assess the potency of HCR-hAAT-codop-FIX, serotype 8 pseudotyped vector was injected into 4-6 week old male C57Bl/6 mice at a dose of 2e9 or 2e10vg/mouse (N=4-6 animals/dose) based on a gel based titration method. FIX expression in murine plasma was assessed by ELISA at 4 weeks after gene transfer in each dose cohort and compared with the levels achieved in identical dose cohorts transduced with HCR-hAAT-FIX, a vector that contains wild type nucleotide sequence in the FIX cDNA. Codon optimisation of the FIX cDNA resulted in a statistically (one sample t test) significant improvement in transgene gene expression at both dose levels as illustrated in FIG. 4.

Next, the inventors compared the potency of single stranded HLP2-TI-codop-FIX with a self-complementary LP1-FIXco expression cassette currently being used in a haemophilia B clinical trial. In brief, both vectors pseudo-typed with serotype 8 capsid were titred using the gel based method to ensure equivalent numbers of self complementary and single stranded AAV particles were administered in 4-8 week old male C57Bl/6 mice. Although transduction with single stranded AAV vectors is limited by the need to convert the single-stranded genome to transcriptionally active double-stranded forms, a head to head comparison showed that for a given vector dose HLP2-TI-codop-FIX mediated at least 3 fold higher levels of FIX in plasma of mice for a given copy of vector in the liver when compared to scAAV-LP1-FIXco (FIG. 6) at 4 weeks after gene transfer, despite the fact that self-complementary vectors are more efficient at forming double stranded transcriptionally active units in the liver.

Sequences

SEQ ID NO. 1—Nucleotide sequence of truncated intron (TI).

SEQ ID NO. 2—Nucleotide sequence of codon optimised FIX. Features: FIX Exon 1: 1-88; FIX Exons 2-5: 89-1386.

SEQ ID NO. 3—Nucleotide sequence of codon optimised FIX containing truncated intron (TI). Features: FIX Exon 1: 1-88; Truncated intron: 89-387; FIX Exon 2-5: 388-1685.

SEQ ID NO. 4—Nucleotide sequence of promoter HLP2.

SEQ ID NO. 5—Nucleotide sequence of HLP2 FIX TI vector. Features: HLP2: 1-354; FIX Exon 1: 425-512; Truncated intron (TI): 513-811; FIX Exons 2-5: 812-2109; bGHpA: 2125-2383.

SEQ ID NO. 6—Nucleotide sequence of codon optimised exons 3 to 5 of FIX.

The invention claimed is:

1. A nucleic acid molecule comprising a promoter, wherein the promoter has a nucleotide sequence having at least 90% identity to the sequence of SEQ ID NO. 4.

2. The nucleic acid molecule of claim 1, wherein the promoter has a nucleotide sequence having at least 91% identity to the sequence of SEQ ID NO. 4.

3. The nucleic acid molecule of claim 1, wherein the promoter has a nucleotide sequence having at least 92% identity to the sequence of SEQ ID NO. 4.

4. The nucleic acid molecule of claim 1, wherein the promoter has a nucleotide sequence having at least 93% identity to the sequence of SEQ ID NO. 4.

5. The nucleic acid molecule of claim 1, wherein the promoter has a nucleotide sequence having at least 94% identity to the sequence of SEQ ID NO. 4.

6. The nucleic acid molecule of claim 1, wherein the promoter has a nucleotide sequence having at least 95% identity to the sequence of SEQ ID NO. 4.

7. The nucleic acid molecule of claim 1, wherein the promoter has a nucleotide sequence having at least 96% identity to the sequence of SEQ ID NO. 4.

8. The nucleic acid molecule of claim 1, wherein the promoter has a nucleotide sequence having at least 97% identity to the sequence of SEQ ID NO. 4.

9. The nucleic acid molecule of claim 1, wherein the promoter has a nucleotide sequence having at least 98% identity to the sequence of SEQ ID NO. 4.

10. The nucleic acid molecule of claim 1, wherein the promoter has a nucleotide sequence having at least 99% identity to the sequence of SEQ ID NO. 4.

11. The nucleic acid molecule of claim 1, wherein the nucleotide sequence of the promoter is the sequence of SEQ ID NO. 4.

12. The nucleic acid molecule of claim 1, wherein the promoter is:
(a) between 330 and 380 nucleotides in length;
(b) between 345 and 365 nucleotides in length; or
(c) between 350 and 360 nucleotides in length.

13. A host cell comprising the nucleic acid molecule of claim claim 1.

14. A pharmaceutical composition comprising the nucleic acid molecule of claim 1 and one or more pharmaceutically acceptable excipients.

* * * * *